United States Patent [19]

Groninger

[11] Patent Number: 4,993,598
[45] Date of Patent: Feb. 19, 1991

[54] PUMP STERILIZATION PROCESS AND PUMPING SYSTEM SUITABLE FOR APPLYING THE PROCESS

[75] Inventor: Horst Groninger, Crailsheim, Fed. Rep. of Germany

[73] Assignee: Groninger & Co. GmbH, Fed. Rep. of Germany

[21] Appl. No.: 351,420

[22] Filed: May 12, 1989

[30] Foreign Application Priority Data

May 18, 1988 [DE] Fed. Rep. of Germany ....... 3816935

[51] Int. Cl.⁵ .................... B67D 5/52; B65B 43/50
[52] U.S. Cl. .................................. 222/148; 141/90; 141/91; 141/147; 141/259; 222/255
[58] Field of Search ............... 222/137, 142, 146.4, 222/148, 255, 262, 267, 275–277, 330, 333–334, 372, 380, 384, 309; 137/241; 141/90–91, 147, 258–259

[56] References Cited

U.S. PATENT DOCUMENTS

| 4,273,263 | 6/1981 | Voegele et al. | 222/148 |
| 4,341,329 | 7/1982 | Kuemmerer et al. | 222/275 |
| 4,353,398 | 10/1982 | Weiler et al. | 141/91 |
| 4,402,428 | 9/1983 | Lang et al. | 222/58 |
| 4,676,279 | 6/1987 | von Lersner | 141/1 |
| 4,711,264 | 12/1987 | Medvid | 137/241 |
| 4,716,921 | 1/1988 | Rangwala et al. | 137/241 |
| 4,759,695 | 7/1988 | Bordini | 222/148 X |

FOREIGN PATENT DOCUMENTS

2081235 2/1982 United Kingdom ............. 141/90

Primary Examiner—Michael S. Huppert
Attorney, Agent, or Firm—Walter A. Hackler

[57] ABSTRACT

A process for the sterilization of pumps for liquid or pasty pharmaceuticals, cosmetics, foodstuffs or similar products, preferably for pumps in which the piston can be driven to slide longitudinally in a cylinder and, at the same time, to rotate about its own axis. The piston contains a recess that reaches as far as the circular cylinder wall and the working face of the piston and communicates with a suction connection in the cylinder wall during a suction stroke and with a pressure connection in the cylinder wall during a pressure stroke and where, further, a closable drainage aperture is preferably provided in the bottom end of the cylinder. A sterilization medium is fed to a pump connection while the pump is being driven. Consequently, the pump does not have to be dismantled for sterilization purposes.

6 Claims, 2 Drawing Sheets

PUMP STERILIZATION PROCESS AND PUMPING SYSTEM SUITABLE FOR APPLYING THE PROCESS

BACKGROUND OF THE INVENTION

The present invention relates to a process for the sterilization of pumps for liquid or pasty pharmaceuticals, cosmetics, foodstuffs or similar, preferably for pumps in which the piston is driven to slide longitudinally and in general vertically within a cylinder and to rotate around its own axis, where the piston contains a recess that reaches as far as the circular cylinder wall and the working face of the piston and communicates with a suction connection in the cylinder wall during a suction stroke and with a pressure connection in the cylinder wall during a pressure stroke and where, further, a closable drainage aperture is preferably provided in the bottom end of the cylinder.

Pumps of this kind, which are mainly used in installations for decanting pasty or liquid pharmaceutical or cosmetical products, have hitherto been sterilized in a dismantled state and under heat and pressure in an autoclave. It is also known for the pump cylinder to be left incorporated in the pump device, but laying the piston bare by withdrawing it through the upper end of the cylinder, and then treating both the piston and the cylinder with a sterilization medium. In the latter case the cylinder must be extended upwards with an enlarged bore and over a distance sufficiently long for it to surround the piston after it has been laid bare. Manufacturing costs are thus increased. In both cases, however, sterilization is associated with additional and costly work. In particular, there is the danger that the sterilized pump will become desterilized during its subsequent assembly.

SUMMARY OF THE INVENTION

The problem underlying the invention is that of simplifying the sterilization process. This problem is solved by feeding a sterilization medium to a pump connection while the pump is actually being driven.

One advantage of the invention consists of the fact that the sterilization medium can be introduced into the pump without the pump first having to be dismantled or laid bare. Rather, even when the sterilization medium is introduced, the pump can be operated in just the same way as it would normally be run, for example, as part of the decanting installation. It has surprisingly been found that when hot steam is used as the sterilization medium, reliable sterilization can be obtained even with the pump still incorporated in its working environment. All the parts of the pump are sufficiently heated and, at one and the same time, the surfaces to be sterilized are brought into sufficiently good contact with moisture. It is another advantage of the invention that the pipelines associated with the pump, i.e. the pipes that during normal operation of the pump carry the products that are being pumped, can likewise be sterilized if the sterilization medium is pumped through the said pipes, something that is particularly easy to realize.

The sterilization medium can be introduced into the pump through the suction connection and then evacuated through the pressure connection. Especially in the case of smaller pumps, say with displacements up to about 25 ml per stroke. It has been found that rapid heating of the pump will be facilitated if the sterilization medium is introduced into the pump through a closable aperture provided in the bottom end of the cylinder. The said aperture can also be advantageously used, at least after sterilization has been terminated, but if necessary also during the sterilization process itself, for withdrawing liquid (condensate) from the pump. (ml=milliliter)

The invention also relates to a pumping system for pharmaceuticals, cosmetics, foodstuffs and similar products with at least one pump in which the piston can be driven to slide longitudinally and in general vertically within a cylinder and to rotate around its own axis, where the piston contains a recess that reaches as far as the circular cylinder wall and the working face of the piston and communicates with a suction connection in the cylinder wall during a suction stroke and with a pressure connection in the cylinder wall during a pressure stroke.

With a view to making the pumping system particularly suitable for the sterilization process according to the invention, provision is made for both piston and cylinder to be made of ceramic materials. Since ceramics have a particularly small thermal expansion, this avoids the danger of the pump seizing during sterilization under the influence of a high temperature when, for example, hot steam is used for this purpose.

An embodiment of the invention provides for the bottom end of the cylinder to be inclined with respect to the horizontal. This facilitates the draining of the sterilization medium.

An embodiment of the invention provides for the cylinder to have a length that essentially corresponds to the length of the piston plus the length of its working stroke. This is possible because the piston does not have to be laid bare. One of the advantages consists of the fact that manufacturing costs are reduced.

One embodiment of the invention provides for the upper end area of the cylinder to terminate in a space that is at least approximately gastight and for a gas connection to lead into this space. By means of this connection it becomes possible to introduce sterile air or some other sterile gas. One advantage consists of the fact that the upper end area of the piston and the cylinder can be protected against the entry of non-sterile environmental air, thus making it even more difficult for germs or contaminating matter to find their way into the pump.

Further features and advantages of the invention follow from the description given below of an embodiment example, complete with a drawing showing essential details of the invention, and from the claims. In any given embodiment of the invention the individual features may be realized either singly or in any desired combination.

DESCRIPTION OF THE PREFERRED EMBODIMENTS

Figure 1:
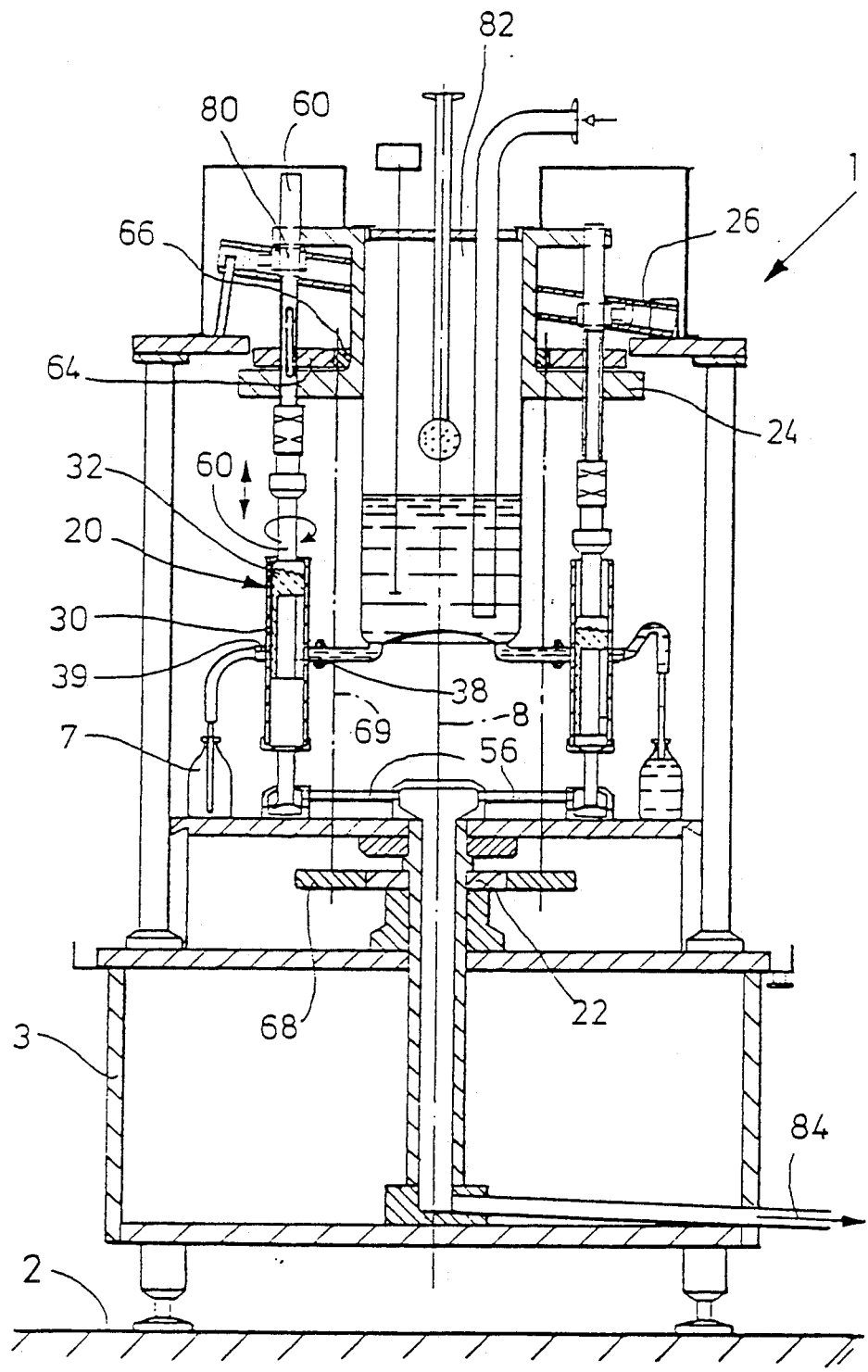
FIG. 1 is a longitudinal section of a decanting machine.

In FIG. 1 a decanting machine 1 for pasty and liquid pharmaceuticals comprises a machine frame 3 resting on a floor 2. In the machine frame 3 a rotary table 6 is mounted and driven rotatably about a vertical axis 8 which is the axis of the machine. The rotary table 6 is provided for receiving containers to be filled, in the example bottles 7. The rotary table constitutes with its radially inner region a carrier for a plurality of pumps 20 rotating with the rotary table 6. Below the rotary table 6 is a gear 22 is mounted coaxially to the axis 8 and is fixedly connected to the frame 3. A machine part 24 in the upper part of the decanting machine is rotatable together with the rotary table 6. In the upper part of the machine frame 3 a guiding rail 26 is arranged provided by a U-profile which is bent to a circular ring which is arranged under an angle relative to the horizontal plane. The angle may be varied in order to adjust the length of the stroke of the pumps 20.

Figure 2:
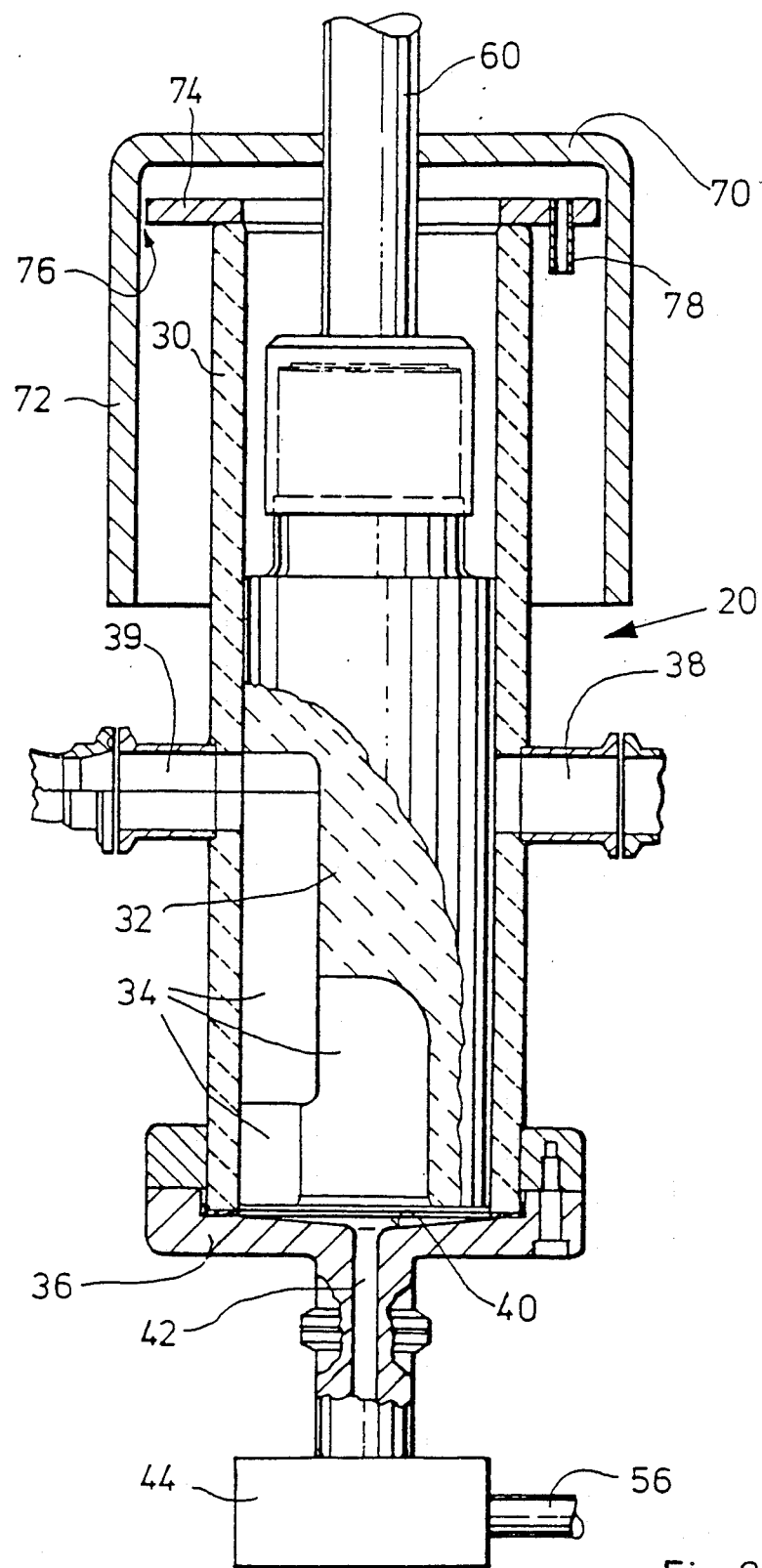
FIG. 2 is a longitudinal section through a pump of the decanting machine.

Each pump 20 (see also FIG. 2) comprises a cylinder 30 having a circular cross-section, made of ceramics and fixed to the revolving table of the machine, in which there is arranged a piston 32, likewise made of ceramics, that can be driven to slide slide along the longitudinal direction of the cylinder, i.e. vertically, and also to rotate about its own axis. The cylinder 30 is fixed on the rotary table 6. The upper part of the piston 32 has a circular full cross section that matches the interior circular shape of the cylinder 30, while in its lower part it has a recess (or cutaway) 34 that extends in the longitudinal direction of the piston and over its length gives access to the internal surface of the cylinder 30 and which also communicates with the central part of a cylinder bottom 36, which is firmly screwed onto the cylinder 30. About halfway along the height of the cylinder and arranged diametrically opposite to each other, the cylinder is provided with a suction connection 38 and a pressure connection 39. The function as suction connection and pressure connection is brought about solely by appropriately combining a longitudinal displacement of the piston with a rotational movement.

The upper side of the cylinder bottom 36 is slightly dished towards its centre, where the bottom 36 is provided with a channel 42 that leads vertically downwards. Screwed to the bottom end of this channel there is a blocking device 44 that, when open, permits the channel 42 to communicate with a drain pipe 56.

The upper end of the piston 32 is connected to a piston rod 60 by means of which the piston is driven in a to and fro motion and, at one and the same time, in a rotational movement always in the same direction. For this purpose, on the piston rod 60 a gliding piece 80 is fixed which engages the guiding rail 26. Further, the piston rod 60 is connected to a gear 64 so as to rotate with the latter but to be able to be shifted in its lengthwise direction relative to the gear 64, and the gear 64 is in driving connection with a gear 66 which is connected via a shaft 69 (only indicated by a dish-dotted line) with 2(a gear 68 which engages the gear 22. The shafts 69 are rotatably mounted in the rotary table 6 and the upper part 24 and, therefore, rotate with the two latter parts. The effective diameters of the gears 64 and 66 have a ratio of 2:1 and the effective diameters of the gears 68 and 22 have a ratio of 1:2. The result is, that with the rotary table 6 rotating and a pump 20 in the left part of FIG. 1 having the shown position of the piston (the piston being totally lifted and the inside of the cylinder being connected with the suction connection 38), after a half rotation of the rotary table 6 the same pump has its piston 32 in the position shown in the right part of FIG. 1 (in its totally lowered position and the cylinder in connection with the pressure connection 39).

A bell 70 (not shown in FIG. 1) closes the upper, open end of the cylinder 30. The bell 70 is fixed to the piston rod 60 and, no matter what the actual operating position of the piston 32, the cylindrical wall 72 of the bell reaches as far as the lower edge of a ring-shaped plate 74 fixed to the upper end of the cylinder 30. The internal diameter of the plate is slightly greater than the internal diameter of the cylinder 30. Between the outer edge of the plate 74 and the cylindrical wall 72 there extends a circumferential air gap 76. By attaching a hose to the connecting nipple provided in the underside of this plate, sterile air or some other sterile gas can be introduced into the bell at a slight overpressure, so that the air or gas will issue from the air gap at a flow velocity of about 0.45 m/s and will thus prevent germs from entering the cylinder from above. No gasket ring made of plastics or similar materials is therefore required. The bell does not increase the overall height of the pump. If necessary, a substantially airtight space as the terminal portion of the upper part of the cylinder can be realized in other ways. In the embodiment example the bell 70 and the plate 74 are made of metal.

During decanting operations the blocking device 44 is maintained in the closed position. During such operations the pasty or liquid products to be pumped will flow from a centrally positioned container 82 to the suction connection 38 of the pump, which will discharge it into the bottles to be filled.

When it becomes necessary to clean (not to sterilize) all the parts of the decanting machine that come into contact with the product that is being handled, the product is removed from its container 82 and replaced by cleaning fluid, which the machine will then continue to pump. In the embodiment example this will be done with the blocking device in its open position. Coming from the suction connection 38 of the pump, the cleaning fluid will thus pass through the entire interior of the pump, including the pressure connection 39 and any other parts connected to it, and will also flow out through the channel 42 in the bottom 36 of the cylinder. The arrangement is dimensioned in such a way that the channel 42 opposes a relatively great resistance to flow, thus avoiding cleaning fluid that has already become fouled from being sucked back into the pump during its suction stroke. If necessary, the blocking device can also be designed as an appropriately controlled valve, so that the channel can be closed during each suction stroke of the pump. The cleaning fluid leaves the machine through a channel 84.

During sterilization, for which the cleaning just described could constitute a preliminary, the sterilization medium — in the example represented by water steam at a temperature of 130°C. and an overpressure of 2 bar — is introduced into the pump for a sterilization time of about twenty minutes.

To this end the sterilization medium must be brought into the pump interior via a connection of the pump and then be removed from it via at least one other connection. Given smaller pumps with displacements up to about 25 ml per stroke, it has been found advantageous to introduce the steam through the central aperture in the bottom of the cylinder and to remove it via the suction and pressure connections. At least at the end of the sterilization, this same aperture in the bottom is used to discharge condensed water from the pump.

In the case of larger pumps, on the other hand, it has been found best to supply the steam via the suction connection and to evacuate through the pressure connection. Here the channel appropriately provided in the bottom of the cylinder is employed for the continual removal of condensate. All the channels through which the hot steam passes become sterilized. It is preferred to introduce the steam into the pumps via the container 82. Thus, also the interior of the container 82 is sterilized. The process according to the invention makes it possible to sterilize also the pipes that lead to and from the pump. Throughout the sterilization process the pump is run in exactly the same way as in normal operation. Thus, the parts in the interior of the pump that come into contact with the products to be handled also come into contact with the superheated steam. Over and above this, the steam will also penetrate into the extremely narrow gap between the piston and the cylinder.

The piston and the cylinder of the pump are made of ceramics with a very low coefficient of thermal expansion, thus avoiding the danger of pump seizure as the result of uneven heating of piston and cylinder.

What is claimed is:

1. Process for the sterilization of pumps for liquid or pasty pharmaceuticals, cosmetics, foodstuffs or similar products, each of said pumps including a piston adapted to slide longitudinally in a cylinder and, at the same time, to rotate about its own axis, the piston including a longitudinal recess adjacent a circular cylinder wall and extending to a working face of the piston, said recess communicating with a suction connection in the cylinder wall during a suction stroke of the piston and with a pressure connection in the cylinder wall during a pressure stroke of the piston said cylinder including a closable drainage aperture in a bottom end thereof said process comprising the step of feeding a sterilization medium to one of the suction and pressure connections while the pump is being driven.

2. The process according to claim 1 further comprising the step of rotating the piston constantly in the same direction as the sterilization medium is fed into one of the suction and pressure connections.

3. A pumping system for liquid or pasty pharmaceuticals, cosmetics, foodstuffs or similar products comprising at least one pump with a ceramic piston disposed with a ceramic cylinder and means for longitudinally sliding the piston in a generally vertical direction within the cylinder and for rotating the piston around a longitudinal axis thereof, the piston containing a recess therein adjacent a circular cylinder wall and extending to a working face of the piston, said recess communicating with a suction connection in the cylinder wall during a suction stroke of the piston and with a pressure connection in the circular cylinder wall during a pressure stroke of the piston, the cylinder including a closable aperture disposed in a bottom of the cylinder.

4. The pumping system according to claim 3 wherein the cylinder bottom is enclosed with respect to the horizontal.

5. The pumping system according to claim 3 wherein the cylinder has a length that essentially corresponds to a length of the piston plus a length of a piston working stroke.

6. The pumping system according to claim 3 wherein an upper end area of the cylinder terminates in a space that is near gastight and the pumping system further comprises a gas connection to the near gastight space.

* * * * *